US006638259B1

(12) United States Patent
Palasis et al.

(10) Patent No.: US 6,638,259 B1
(45) Date of Patent: Oct. 28, 2003

(54) BIOCOMPATIBLE MEDICAL DEVICES

(75) Inventors: Maria Palasis, Wellsley, MA (US); Louis Ellis, St. Anthony, MN (US); Timothy Mickley, Elk River, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/429,178

(22) Filed: Oct. 28, 1999

(51) Int. Cl.$^7$ .............................................. A61M 25/00
(52) U.S. Cl. ...................................... 604/264; 604/265
(58) Field of Search .......................... 604/890.1, 891.1, 604/892.1, 130–13, 264–266, 265; 623/1.44, 1.46; 427/2.12, 2.25

(56) References Cited

U.S. PATENT DOCUMENTS

| | | | | |
|---|---|---|---|---|
| 2,814,296 A | * | 11/1957 | Everett | 604/265 |
| 3,358,684 A | * | 12/1967 | Marshall | 604/265 |
| 3,598,127 A | * | 8/1971 | Wepsic | 604/265 |
| 4,589,873 A | * | 5/1986 | Schwartz et al. | 604/265 |
| 4,999,210 A | * | 3/1991 | Solomon et al. | 427/2 |
| 5,098,977 A | | 3/1992 | Frautschi et al. | 527/313 |
| 5,266,359 A | * | 11/1993 | Spielvogel | 427/388.4 |
| 5,368,048 A | * | 11/1994 | Stoy et al. | 128/772 |
| 5,468,562 A | * | 11/1995 | Farivar et al. | 428/457 |
| 5,492,763 A | * | 2/1996 | Barry et al. | 428/457 |
| 5,891,507 A | * | 4/1999 | Jayaraman | 427/2.25 |
| 5,928,216 A | * | 7/1999 | Spencer | 604/523 |
| 5,947,940 A | * | 9/1999 | Beisel | 604/282 |
| 5,997,517 A | * | 12/1999 | Whitbourne | |
| 6,059,738 A | * | 5/2000 | Stoltze et al. | 600/585 |
| 6,080,488 A | * | 6/2000 | Hostettler et al. | 428/423.3 |
| 6,096,070 A | * | 8/2000 | Ragheb et al. | 623/1 |
| 6,120,536 A | * | 9/2000 | Ding et al. | 623/1.43 |
| 6,315,792 B1 | * | 11/2001 | Armstrong et al. | 623/1.23 |

FOREIGN PATENT DOCUMENTS

| | | | |
|---|---|---|---|
| EP | 0 798 398 A2 | 10/1997 | |
| WO | WO 92/05829 | 4/1992 | A61M/29/00 |
| WO | WO 94/16836 | 8/1994 | B08B/3/12 |
| WO | WO 98/40469 | 9/1998 | C12N/5/12 |
| WO | WO 98/53762 | 12/1998 | A61F/2/06 |
| WO | WO 99/62395 | 12/1999 | |
| WO | WO 00/76573 A1 | 12/2000 | A61M/31/00 |

* cited by examiner

Primary Examiner—Sharon Kennedy
(74) Attorney, Agent, or Firm—Mayer Fortkort & Williams, PC; David B. Bonham, Esq.

(57) ABSTRACT

A modified medical device for delivery of a pharmaceutically active material is described. The present inventors have found that many conventional medical devices contain a metallic component that comes into contact with a pharmaceutically active material during use, and that the contact substantially reduce the pharmaceutical effectiveness of the pharmaceutically active material. The invention described herein concerns numerous modifications to the metallic component that are effective to prevent such a substantial reduction in pharmaceutical effectiveness.

15 Claims, 9 Drawing Sheets

FIG. 6

Effect of BSA flush on virus activity

Virus titer (PFU/ML)

- Control
- Injection catheter
- BSA flushed injection catheter

BIOCOMPATIBLE MEDICAL DEVICES

FIELD OF THE INVENTION

The present application relates to medical devices for delivery of pharmaceutically active materials. More specifically, the present invention relates to methods and compositions effective to prevent reduction in the activity of pharmaceutically active materials arising from contact with metallic components of medical devices.

BACKGROUND OF THE INVENTION

Medical devices having metallic components are used extensively in the medical field. In many cases the medical device is used for delivery of a pharmaceutically active material, and the pharmaceutically active material comes into contact with the metallic component during the course of delivery of the pharmaceutically active material. For example, metallic lumens are frequently used to carry pharmaceutically active materials to various bodily tissues. As another example, metallic stents having a drug delivery polymer coating thereon are used for delivery of pharmaceutically active materials. In both examples, the pharmaceutically active material contacts the metallic component. Metallic components such as stainless steel and nickel-titanium superelastic alloys (e.g., nitinol), cobalt based alloys and super-alloys are commonly used for this purpose as they are formable, have desirable mechanical properties and are commonly believed to be substantially inert.

The present inventors, however, have found that such materials are incompatible with certain pharmaceutically active materials. As a result, there is at present a need in the art to overcome this incompatibility.

BRIEF DESCRIPTION OF THE DRAWINGS

FIG. 6 presents absolute virus titer (log scale) after 30 minute incubation for the following: (a) control, (b) an untreated injection catheter constructed of stainless steel and nitinol, and (c) an injection catheter constructed of stainless steel and nitinol treated with a BSA flush.

SUMMARY OF THE INVENTION

Figure 1:
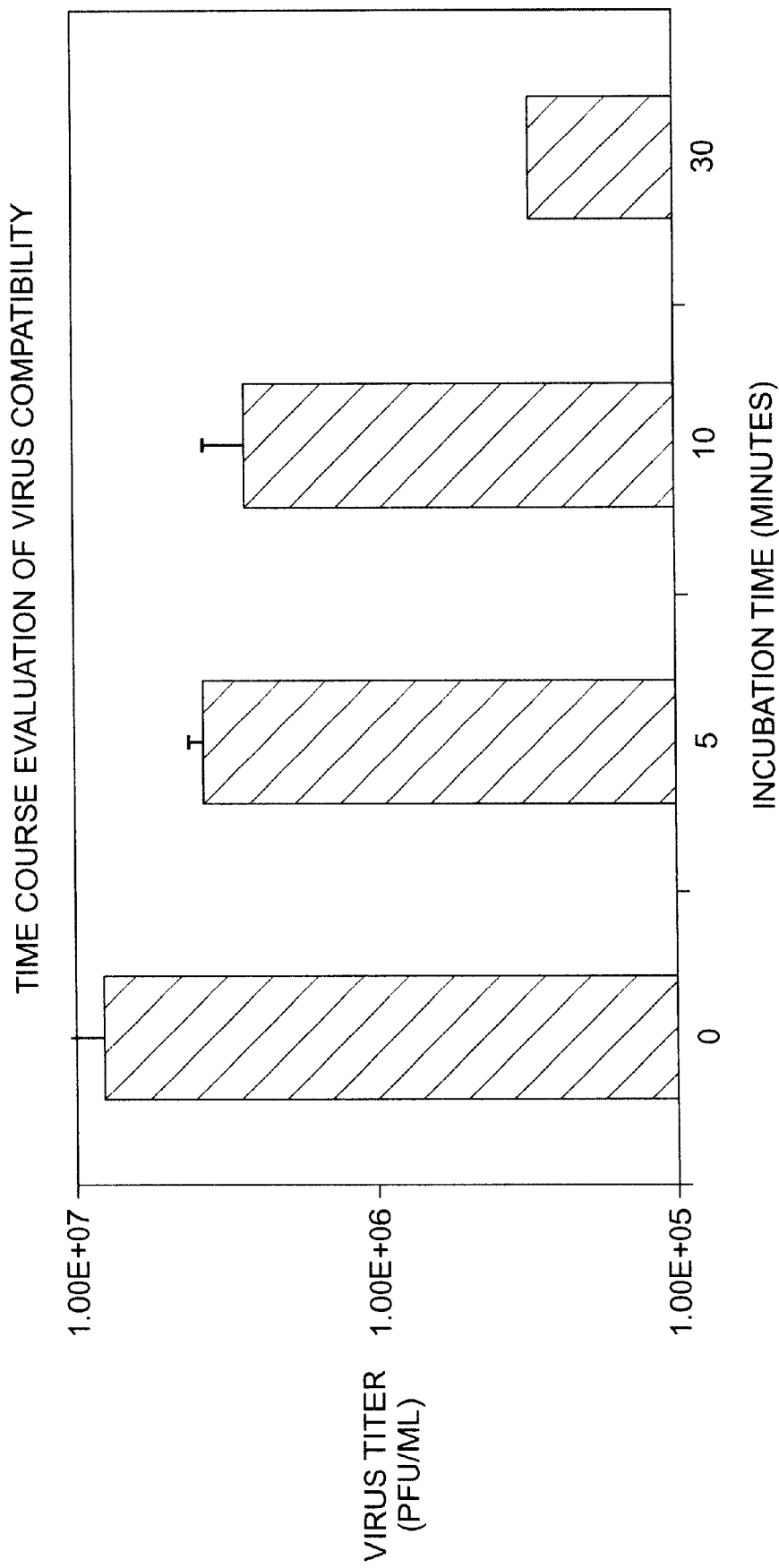
FIG. 1 presents absolute virus titer (log scale) as a function of time for an untreated injection catheter.

According to an embodiment of the invention, a method and modified medical device for delivery of a pharmaceutically active material are provided. The medical device comprises a conventional medical device having a metallic component which comes into contact with a pharmaceutically active material during use, such contact acting to substantially reduce the pharmaceutical effectiveness of the pharmaceutically active material. The metallic component is modified to prevent this substantial reduction in pharmaceutical effectiveness in accordance with the invention.

Numerous devices benefit from the present invention, including medical devices comprising a metallic lumen, such as hypodermic needles and intravascular catheters having an injection lumen, and medical devices that do not have a lumen, such as metallic stents coated with polymer for delivery of the pharmaceutically active material. Examples of metallic components resulting in a substantial reduction in pharmaceutical effectiveness include stainless steel and nitinol. Pharmaceutically active materials benefiting from the present invention include materials comprising polynucleotides, such as viral vectors, proteins, whole cells, small and large molecule drugs, and so forth.

According to one aspect of the invention, the metallic component is modified by providing it with a surface treatment. Appropriate surface treatments include chemical passivation treatments, such as acid treatment (e.g., treatment with citric acid, nitric acid, etc.) and treatment with steam. Other appropriate surface treatments include treatment with a pharmaceutically acceptable protein, such as albumin, or treatment with a layer of polymeric material, such as polyethylene, polypropylene, polytetrafluoroethylene, and so forth. In some embodiments, the polymer is provided as a preformed composition, in other embodiments, the polymer is applied in an uncured form, such as a liquid form, and cured. Still other appropriate surface treatments include treatment with a layer of inorganic material, such as carbon, for example, by means of chemical vapor deposition. Yet other surface treatments involve providing the metallic component with a layer of a more inert metallic material, such as titanium or platinum.

In other embodiments the metallic component is replaced, for example, with a more inert metallic component, such as titanium and platinum, or with a polymeric component, such as polyethylene, polypropylene, polytetrafluoroethylene, poly ether ether ketone or polyimide.

One advantage of the present invention is that incompatibility problems that are presently experienced when metallic components of medical devices come into contact with pharmaceutically active materials are minimized.

Another advantage is that the pharmaceutical effectiveness of pharmaceutically active materials that come into contact with metallic components is not substantially decreased.

Still other embodiments and advantages will become readily apparent to those skilled in the art upon review of the Detailed Description, Examples and Claims set forth below.

DETAILED DESCRIPTION

At present, many medical devices are known in which pharmaceutically active materials pass through metallic lumens or otherwise come into contact with metal prior to delivery to tissue. However, as seen from the examples below, the present inventors have found that where pharmaceutically active materials contact certain metallic substrates, pharmaceutical effectiveness is substantially reduced relative to the same materials, which have not come into contact with such substrates. Specifically, the present inventors have found that where viral particles contact metallic materials, such as stainless steel and/or nickel-titanium superalloys such as nitinol, viral transfection is substantially reduced, apparently due to inactivation of the virus. This is surprising, since it is normally assumed that such materials are relatively inert and hence unlikely to interact with a pharmaceutically active material.

By "substantially reduced" or "substantial reduction" is meant that pharmaceutical effectiveness is reduced, for example, by at least 5%, more preferably 10%, 20%, or more. By "pharmaceutical effectiveness" or "pharmaceutical efficacy" is meant any desired pharmaceutical pharmacological result. For example, a virus having a 10% reduction in pharmaceutical effectiveness is able to infect 10% less cells than it otherwise would. As another example, the pharmaceutical effectiveness of a protein can be measured by its activity through an Elisa assay.

The present invention overcomes the above and other difficulties by providing medical devices for delivery of pharmaceutically active materials in which the metallic components of such devices that come into contact with the pharmaceutically active materials are modified. The devices of the present invention thus do not result in a substantial reduction in pharmaceutical effectiveness.

Conventional (i.e., known) medical devices benefiting from the present invention are numerous and include, for example, catheters, conventional needle syringes, hypodermic needles, biopsy needles and devices, tissue ablation devices, needle injection catheters (for endocardial, epicardial, and pericardial agent administration), filters, grafts, stents including those having a polymer coated thereon for delivery of pharmaceutically active materials, aneurysm filling coils, transmyocardial revascularization devices, percutaneous myocardial revascularization devices, soft tissue clips, sutures, blood clot filters, and so forth. Specific examples of devices for drug delivery to the heart include, for example, those found in the following patents and patent applications: U.S. Pat. Nos. 5,450,846, 5,840, 059, 5,878,751, 5,551,427, 5,931,834, 5,925,012, 5,925,033, 5,538,504, WO 99/39624, WO 99/44656, WO 99/21510, WO 99/29251, EP A 99-06 0895752, and EP A 99-01 0888750, each of which is incorporated herein by reference.

The medical devices contemplated for use in connection with the present invention can be used for systemic treatment or to treat any mammalian tissue or organ. Non-limiting examples include tumors; organs including but not limited to the heart, lung, brain, liver, kidney, bladder, urethra and ureters, eye, intestines, stomach, pancreas, ovary, prostate; skeletal muscle; smooth muscle; breast, cartilage and bone. The terms "pharmaceutically active materials", "therapeutic agents" and "drugs" are used interchangeably herein and include pharmaceutically active compounds, polynucleotides with and without carrier vectors such as lipids, compacting agents (such as histones), cells, virus, virus-like particles, polymers, proteins, enzymes, small and large molecule drugs, and the like, with or without targeting sequences. An injection administered in accordance with the present invention includes the pharmaceutically active material and solutions thereof. Pharmaceutically active materials useful in accordance with the present invention may be used singly or in combination.

A "polynucleotide" is a nucleic acid molecule polymer, such as DNA, RNA and their analogs, having as few as 3 nucleotides, and can include both double- and single-stranded sequences. A "protein" is a polymer of as few as two (dimer) amino acid residues. Preferably, the pharmaceutically active material is a polynucleotide.

Specific examples of pharmaceutically active materials used in conjunction with the present invention include, for example, pharmaceutically active compounds, cells, proteins, oligonucleotides, ribozymes, antisense oligonucleotides, DNA compacting agents, gene/vector systems (i.e., any vehicle that allows for the uptake and expression of nucleic acids), polynucleotides (including, for example, recombinant nucleic acids; naked DNA, cDNA, or RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposome and cationic polymers that are selected from a number of types depending on the desired application. Cells can be of human origin (autologous or allogeneic) or from an animal source (xenogeneic), genetically engineered if desired to deliver proteins of interest at the transplant site. The delivery media can be formulated as needed to maintain cell function and viability.

Several therapeutic categories and exemplary pharmaceutically active materials follow. Examples include anti-inflammatory agents such as dexamethasone, prednisolone, corticosterone, budesonide, estrogen, sulfasalazine, mesalamine, and analogues thereof; antineoplastic/antiproliferative/anti-miotic agents such as paclitaxel, 5-fluorouracil, cisplatin, vinblastine, vincristine, epothilones, endostatin, angiostatin, thymidine kinase inhibitors, and analogues thereof; anesthetic agents such as lidocaine, bupivacaine, ropivacaine, and analogues thereof; anti-coagulants; integrins, chemokines, cytokines and growth factors.

According to one embodiment of the invention, the metallic component of the medical device is modified by providing it with a surface treatment. All methods of the present invention, including surface treatments, act to prevent a substantial reduction in pharmaceutical efficacy of the pharmaceutically active material.

One form of surface treatment in accordance with the present invention is a chemical passivation treatment. Preferred chemical passivation treatments include those that provide a robust oxide barrier, such as acid treatment and treatment with steam at high temperature. Preferred acids for this purpose include citric acid, nitric acid, and chromic acid. According to an especially preferred embodiment, the metallic component is treated with acid, immediately followed by treatment with steam at high temperature (e.g., by autoclaving). Information concerning chemical passivation of stainless steel can be found, for example, in ASTM Designation: A 967–96 entitled "Standard Specification for Chemical Passivation Treatments for Stainless Steel Parts," the entire disclosure of which is hereby incorporated by reference. Procedures are set forth therein for nitric acid treatment, citric acid treatment, as well as other treatments, including electrochemical treatments.

Other forms of surface treatment include treating the metallic component with pharmaceutically acceptable solutions such as a saline or suitable buffer wash (phosphate buffered saline); lipids; emulsifying agents and detergents such as glycerin, sodium lauryl sulfate, sodium oleate; proteins, such as, for example, albumin, particularly human serum albumin (HSA), and bovine serum albumin (BSA); other natural polymers such as hyaluronic acid and collagen; synthetic polymers such as polyethylene glycol, polyethylene oxide and polytetrafluoroethylene; and so forth. Treatment may also be carried out by formulating the agents mentioned above directly into the solution containing the therapeutic agent. For instance, human serum albumin may be formulated into a viral solution such as adenovirus in order to exert a desired effect. Additionally, the surface treatment may concurrently involve a cleaning process and/or sterilization process to remove surface contaminants or impurities.

Still other forms of surface treatment involve formation of an inorganic layer, for example, amorphous carbon, other diamond-like coatings, or silicone carbide. A preferred method of forming such inorganic layers is chemical vapor deposition (CVD) or physical vapor deposition (PVD).

Hence, in the case of certain polymeric and other materials of suitable mechanical character, the surface treatment may simply involve the application of a preformed material. As an example, in the case of a metallic lumen, the metallic surface can be treated by simply inserting a preformed tube of polymeric material into the metallic lumen.

Moreover, polymers and other materials can be formed on the metallic substrate by any suitable means, such as dipping, spraying, vapor deposition, plasma polymerization and so forth. In many embodiments, a liquid layer is solidified. For example, in the case of polymers, the metallic surface can be treated by forming a polymer layer on the metallic component from a liquid layer. Exemplary embodiments for the formation of polymer layers from a liquid layer include (1) formation of a solvent dispersion of a polymer of interest, then coating a surface of the metallic component with the dispersion, followed by removal of solvent, and (2) first coating a surface of the metallic component with a curable polymer resin and subsequently curing the resin, for example, with ultraviolet or infrared radiation.

Hence, polymers appropriate for the practice of the invention include preformed and unformed polymers. Polymers may be crosslinked or uncrosslinked, natural or synthetic, biostable, biodegradable, or dissolvable. These materials may be selected from numerous polymers known in the art. Exemplary polymers are selected from polycarboxylic acids, cellulosic polymers including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA (ethylene-vinyl acetate copolymer), polyvinyl ethers, polyvinyl aromatics, polyethylene oxides, glycosaminoglycans, polysaccharides, polyesters including polyethylene terephthalate, polyacrylamides, polyethers, polyether sulfone, poly ether ether ketones, polyamides, polycarbonate, polyalkylenes including polypropylene, polyethylene and high molecular weight polyethylene, ethylene vinyl acetate polymers, halogenated polyalkylenes including polytetrafluoroethylene, polyurethanes, polyorthoesters, proteins, polypeptides, silicones, styrene-butadiene polymers, polyimides, polylactic acid, polyglycolic acid, polycaprolactone, polyhydroxybuterate valerate and blends and copolymers thereof as well as other biodegradable, bioabsorbable and biostable polymers and copolymers. Thermoplastic elastomers such as polyether block amides and styrene-butadiene-styrene. Coatings from polymer dispersions such as polyurethane dispersions (BAYHYDROL, etc.) and acrylic latex dispersions are also within the scope of the present invention. The polymer may be a protein polymer, fibrin, collagen, derivatives of these polysaccharides, an extra cellular matrix component, hyaluronic acid, or another biologic agent or a suitable mixture of any of these, for example. In one embodiment, the polymer is polyacrylic acid, available as HYDROPLUS (Boston Scientific Corporation, Natick Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another embodiment, the polymer is a copolymer of polylactic acid and polycaprolactone.

Preferred polymers include polyethylene, polyethylene terephthalate (PET), ethylene vinyl acetate polymers, polypropylene, silicone polymers, polyurethanes, styrene-butadiene polymers, fluorinated polyalkenes such as polytetrafluoroethylene (PTFE), polyimides, poly ether ether ketones (PEEK), polyamides, etc. More preferred polymers include polypropylene, polyethylene and fluorinated polymers such as PTFE, polyvinylidene fluoride (PVDF).

Polymers may be hydrophobic or hydrophilic. Hydrophobic polymers are preferred in connection with hydrophilic pharmaceutically active materials because hydrophobic interactions between two hydrophobic molecules are avoided. Similarly, hydrophilic polymers are preferred in connection with hydrophobic materials. Moreover, polymers holding a charge similar to that of the biologically active material will tend to interact less with, and hence may tend to be more inert to, a pharmaceutically active material, due to repulsive forces. However, this will be highly dependent on the particular therapeutic agent to be delivered.

In general, favorable interactions (e.g., ionic, van der Waals, hydrophobic, etc) between the material and therapeutic agent should be reduced such as to avoid adsorption of the therapeutic agent onto the surface or inactivation or denaturation by the surface. In other embodiments, the metallic component is replaced. Exemplary embodiments include replacement of the metallic component with a polymeric component such as those previously discussed. As above, the polymer should be compatible with the pharmaceutically active material and, of course, the subject into which the pharmaceutically active material is to be introduced. Moreover, the polymer should meet any structural requirements. Numerous methods are available to provide structural integrity or flexibility.

For example, in the event that the medical device comprises a needle (or cannula) for delivery of the pharmaceutically active material, a polymeric needle can be fashioned from several of the materials listed above, notably polyimide, PTFE, PET, polyphenylene sulfide (PPS), polysulfone (PS) and PEEK, which have excellent rigidity and the ability to be sharpened into a needle. Additional materials are disclosed in U.S. Pat. No. 4,838,877, including, polycarbonates, polyetherimides, polymethylpentenes, polyesters, acrylates, polyaramides, polyamides, modified phenylene oxides, and polysulfones. Alternatively, where enhanced strength and/or rigidity are desired, the polymeric material can be reinforced, for example, by fibers. For example, U.S. Pat. No. 5,637,399 discloses a synthetic resin needle of reinforced with combustible fibers whose longitudinal directions are arrayed straight or curvilinearly along the axial length of the needle. Resins listed include: cyclic olefinic resin, polyphenylene sulfide, polyether etherketone, polybutylene terephthalate, polycarbonate, polyamide, polyacetal, modified polyphenylene ether, polyester resin, polytetrafluoroethylene, fluorine plastic, polysulfone, polyester imide, polyether sulfone, polyether ketone, polyether lactone, crystalline polyester, polyamide imide, polyimide, and thermosetting resins such as epoxy resin, unsaturated polyester resin, phenol resin, urea resin, melamine resin and polyurethane resin. Metal or ceramic reinforcements are included in addition to combustible fibers.

In still other embodiments, a metallic component is replaced or coated with a substantially more inert metal. For example, stainless steel or nickle-titanium alloys (e.g. nitinol) may be coated with titanium or platinum. Alloys may also be replaced with pure metals.

It is noted that, where a pharmaceutically active material is provided in liquid form, and where liquid is subjected to substantial shear forces, such as in the case of a narrow lumen, the pharmaceutically active material may undergo mechanical damage, particularly if it is in the form of a biomolecule, such as a virus or protein. Methods of reducing such shear forces include (1) enlarging the widths of internal flow paths (e.g., enlarging inner diameters), (2) providing a smoother surface finish, for example, by etching, honing or otherwise mechanically smoothing internal surfaces, (3) by reducing the viscosity of the liquid, (4) by decreasing the flow rate of the liquid, and so forth.

Below are examples of specific embodiments for carrying out the present invention. The examples are offered for illustrative purposes only, and are not intended to limit the scope of the present invention in any way.

70% confluency the day before the experiment. Prior to contacting the HeLa cells, the viral solution was diluted appropriately in infection media (DMEM (Dulbecco's Modified Eagle's Medium)+2% FBS(Fetal Bovine Serum)) to achieve a result of 1E+02–1E+03 infected cells per well. The diluted virus was added to the HeLa cells in the wells and incubated at 37° C. for 1 hour. 5 mls of DMEM+10% FBS were then added to each well, followed by incubation for 24–30 hours at 37° C. After aspirating of the media, the cells were fixed in 0.5% glutaraldehyde in PBS (phosphate buffered saline) for 10 minutes. The cells were washed twice in PBS and stained using an X-gal staining solution overnightat 37° C. (X-gal is 5-bromo-4-chloro-3-indolyl-$\beta$-D-galactoside, which is hydrolyzed by $\beta$-galactosidase to form a blue product). Blue cells were counted the next day to determnine the titer.

Data are presented in the table to follow for 0 (simple flush through), 5, 10 and 30 minutes in the catheter. The data are presented in the table in terms of cell counts (accounting appropriately for dilution), in terms of absolute titer (pfu/ml), and in terms of percentage of the titer of stock virus (3.0E+07 pfu/ml).

Figure 2:
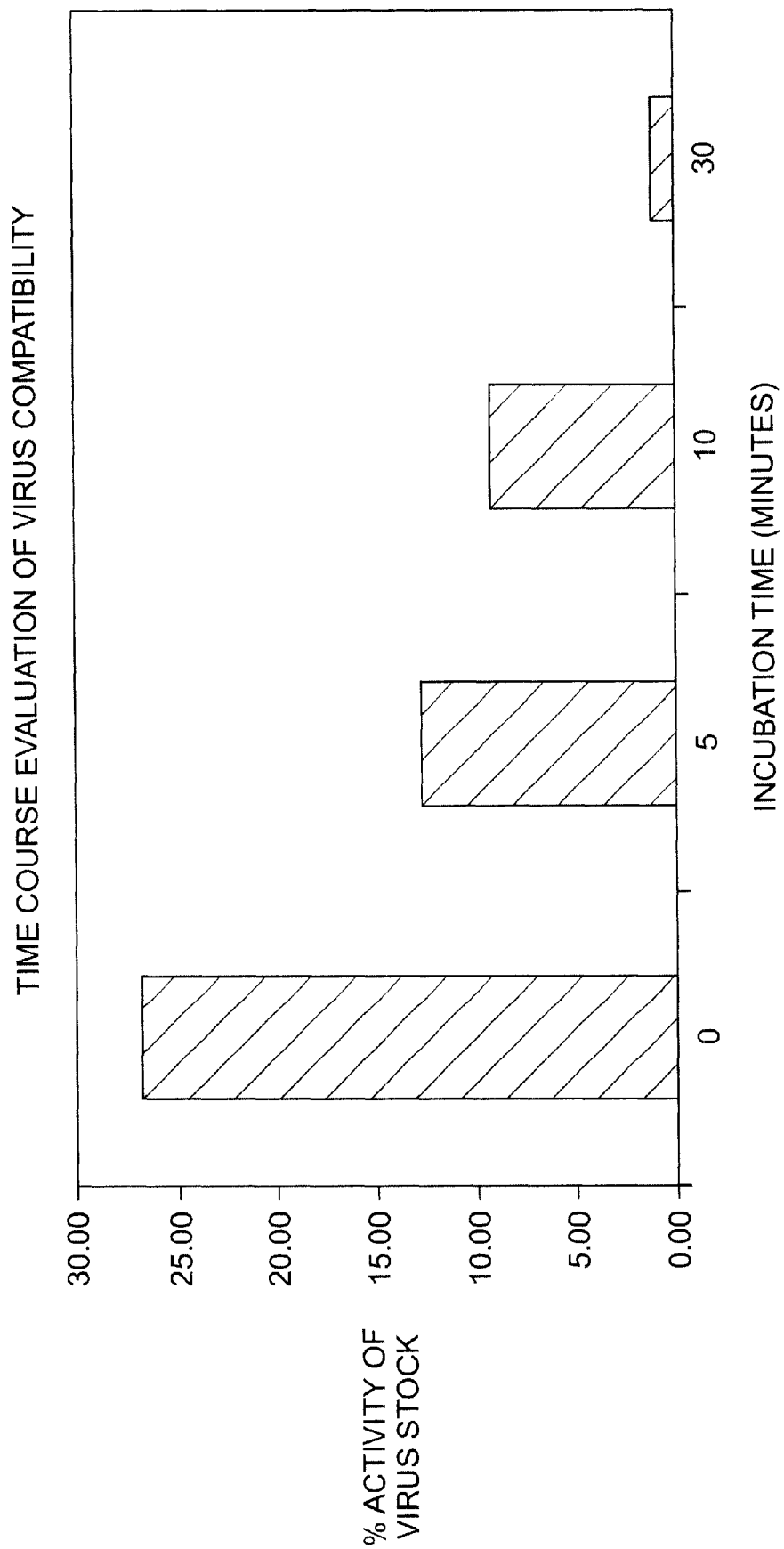
FIG. 2 presents the data of FIG. 1 as a percentage of viral stock titer (linear scale).

FIG. 1 presents these data in terms of absolute virus titer (log scale) and FIG. 2 presents these data relative to the viral stock titer (linear scale). These data suggest that residency in the catheter results in a deterioration of viral efficacy and that this deleterious effect increases with increasing exposure time.

| Time (min.) | Pos. Cells #1 | Pos. Cells #2 | Pos. Cells #3 | Titer (pfu/ml) | Std. Dev. | % of stock |
|---|---|---|---|---|---|---|
| 0 | 7400000 | 10800000 | 5900000 | 8.03E+06 | 2.51E+06 | 26.78 |
| 5 | 3400000 | 4100000 | | 3.75E+06 | 4.95E+05 | 12.50 |
| 10 | 3900000 | 2400000 | 1800000 | 2.70E+06 | 1.08E+06 | 9.00 |
| 30 | 300000 | 300000 | 300000 | 3.00E+05 | 0.00E+00 | 1.00 |

EXAMPLES

Example 1

Time Course Evaluation of Virus Compatibility

A CMV-$\beta$-gal adenovirus (i.e., an adenoviral vector driven by a CMV (cytomegalovirus) promoter and encoding a $\beta$-galactosidase ($\beta$-gal) reporter gene) was used as a stock virus in this example.

Stock virus having a viral titer of $3 \times 10^7$ (also referred to herein as 3E+07) plaque-forming units/ml (pfu/ml) was incubated in catheters at 37° C. The catheters used were endocardial catheters like those described in international patent application WO/9922655, the disclosure of which is hereby incorporated by reference in its entirety. These catheters have a proximal portion formed from heat-treated stainless steel and a distal portion formed from a nitinol hypotube (referred to in these examples as "catheter" or "injection catheter"). After the allotted amount of time (0–30 minutes, where 0 minutes refers to the situation in which the viral solution was flushed through the catheter), the viral solution was pushed through the catheter into a polypropylene eppendorf tube. The viral solution was then titered on HeLa cells (human epidermoid carcinoma cells). For this purpose, HeLa cells were first plated out in well plates at Example 2

Time Course Evaluation of Virus Compatibility

Procedures similar to Example 1 were followed, except that an additional initial viral titer (4E+08 pfu/ml) was examined, both in a catheter and as a control. For the control, the virus was exposed to a polypropylene vial for the appropriate period.

The number of positive cells was counted:

(a) after 0 (flush through) and 30 minutes in the control vial (4E+08 pfu/ml), (b) after 0 (flush through) and 30 minutes in the catheter, using the same stock virus titer as the control (4E+08 pfu/ml), and (c) after 0 (flush through) and 30 minutes in the catheter, using a lower stock virus titer (3E+07 pfu/ml).

Figure 3:
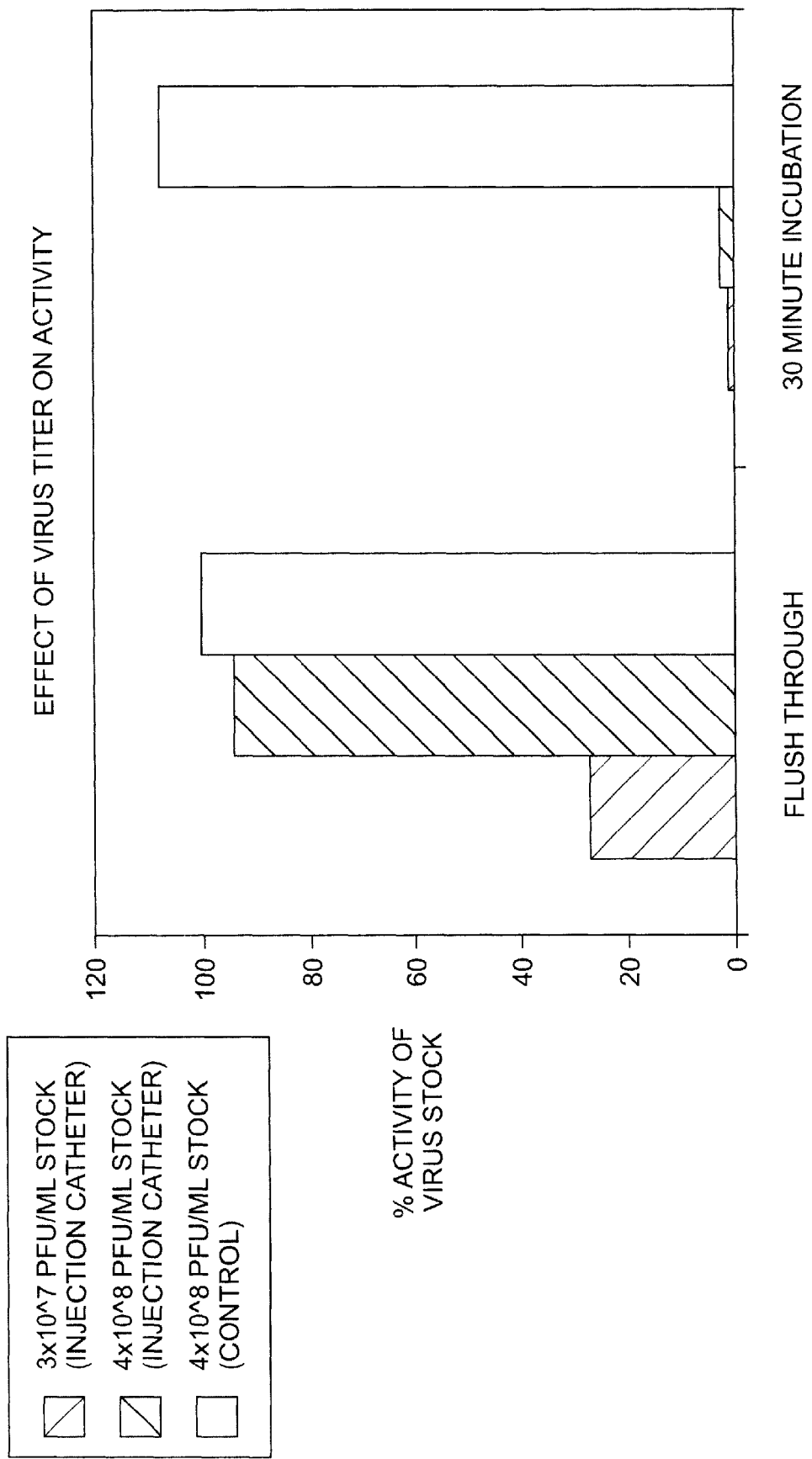
FIG. 3 presents virus titer (as a percentage of virus stock titer): (a) after 0 (flush through) and 30 minutes for a control (4E+08 pfu/ml initial titer), (b) after 0 (flush through) and 30 minutes for an injection catheter constructed of stainless steel and nitinol, using the same stock virus titer as the control (4E+08 pfu/ml initial titer), and (c) after 0 (flush through) and 30 minutes for an injection catheter constructed of stainless steel and nitinol, using a lower stock virus titer (3E+07 pfu/ml initial titer).
Figure 4:
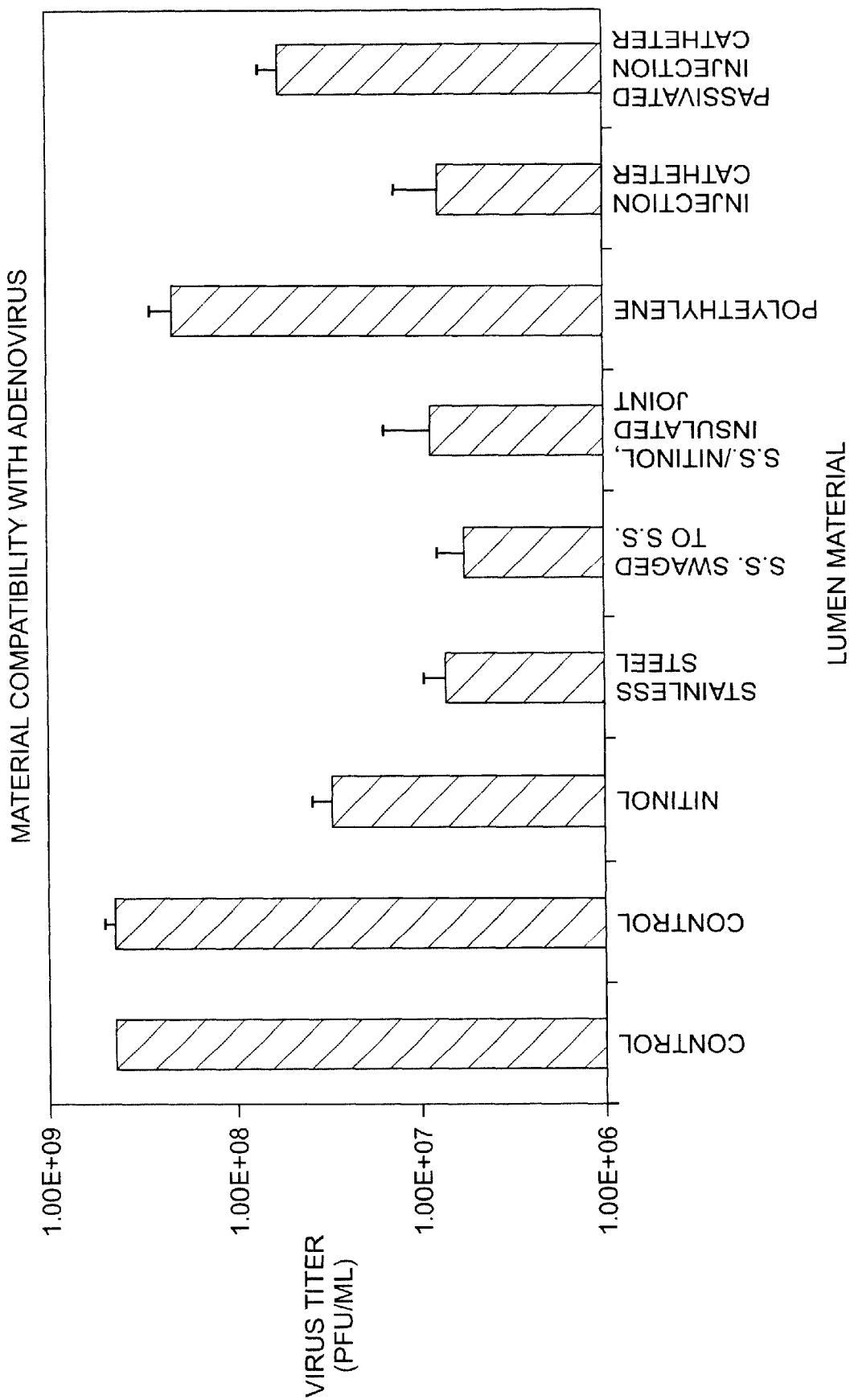
FIG. 4 presents absolute virus titer (log scale) after 30 minute incubation in the following materials: a nitinol lumen, a stainless steel lumen, a lumen of stainless steel swaged to nitinol, a lumen of stainless steel swaged to nitinol with an insulated joint, a polyethylene lumen, an injection catheter constructed of stainless steel and nitinol, and a passivated injection catheter constructed of stainless steel and nitinol.
Figure 5:
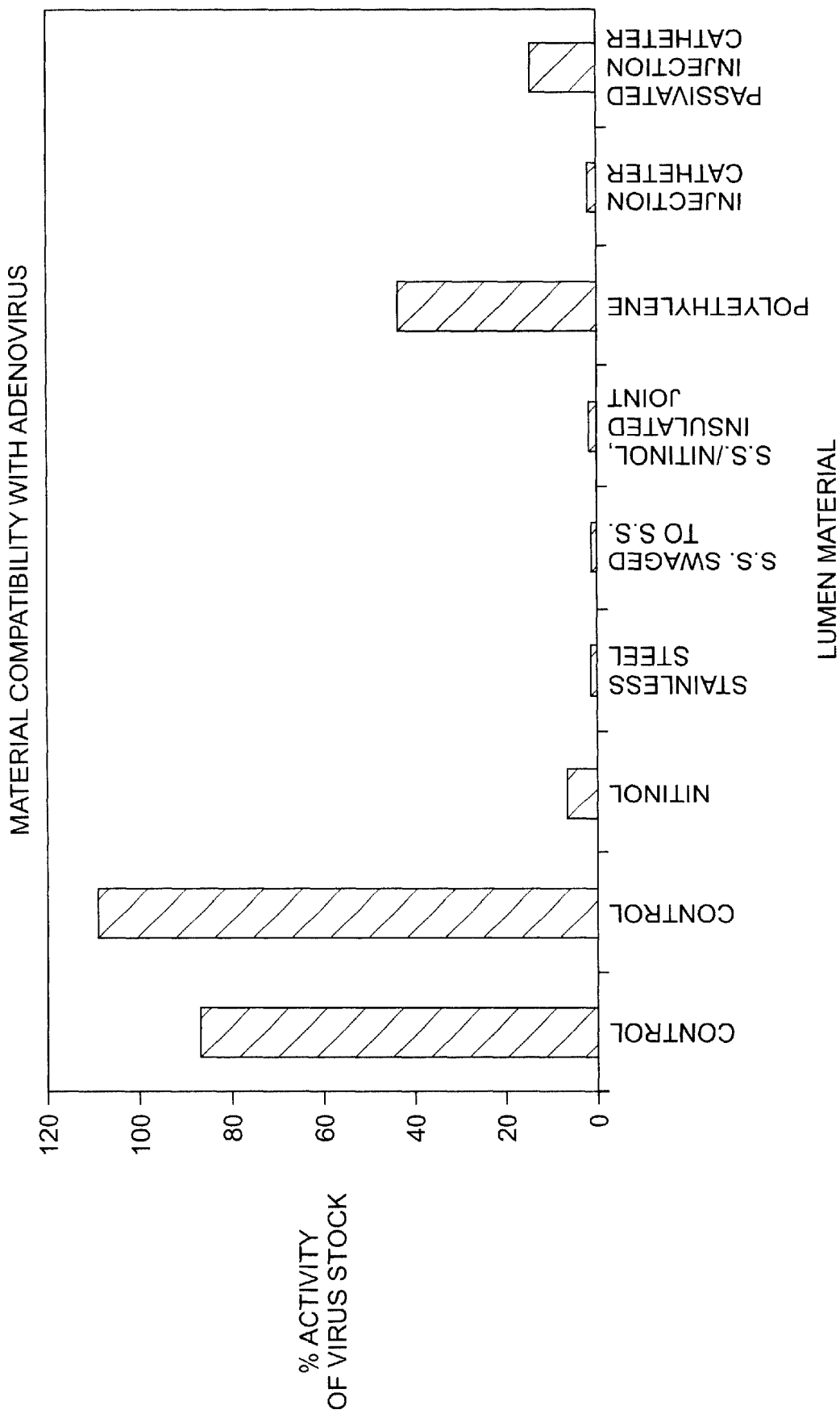
FIG. 5 presents the data of FIG. 4 as a percentage of viral stock titer (linear scale).

Data are presented in the tables to follow. FIG. 3 presents these data as a percentage of viral stock titer. As in Example 1, there is a significant drop in virus activity as a function of incubation time. For a virus stock titer of 3E+07 pfu/ml, a flush through resulted in a 75% loss of activity relative to the viral stock while a 30-minute incubation resulted in a 99% loss of activity. At the higher titer of virus, 4E+08 pfu/ml, a flush through the catheter resulted in only a 6% loss of activity. However, 97% activity was lost after 30 minutes, consistent with the results at the lower titer. Hence, simply increasing viral titer does not appear to be an effective solution to the loss in viral efficacy observed.

TABLE

Catheter time course evaluation (viral stock titer 4E+08).

| Time | Positive cells | Positive cells | Positive Cells | Titer (pfu/ml) | std dev | % of stock |
|---|---|---|---|---|---|---|
| 0 | 400000000 | 330000000 | 400000000 | 3.77E+08 | 4.04E+07 | 94.17 |
| 30 | 4000000 | 12000000 | — | 8.00E+06 | 5.66E+06 | 2.67 |

TABLE

Time course evaluation.

| Initial Virus Titer (pfu/ml stock) | Flush through | 30 minute incubation |
|---|---|---|
| 3E + 07 (catheter) | 26.78 | 1 |
| 4E + 08 (catheter) | 94.17 | 2.67 |
| 4E + 08 (control) | 100 | 108 |

Example 3

Material Compatibility

In this example, the procedures of Example 1 were followed, except viral titers were measured after exposure to various materials for 30 minutes. In some examples, a stock viral titer of 5E+08 was used. In others, marked with "*" in the table below, a stock viral titer of 4E+08 was used. For a control, the stock virus was placed in a polypropylene vial for 30 minutes.

Lumen materials for this example were as follows: nitinol, stainless steel, stainless steel swaged to nitinol, stainless steel swaged to nitinol with an insulated joint, polyethylene, an injection catheter constructed of stainless steel/nitinol (see above), and a passivated injection catheter. The passivation process was conducted as set forth in ASTM standard A967-96 "Chemical passivation of stainless steel parts". Specifically, the catheter was treated with a 7% weight to volume citric acid solution in water for 7 minutes at 70° C. Immediately after removal from the citric acid solution, the catheter was thoroughly rinsed in water multiple times.

Absolute titers are presented in FIG. 4 (log scale), and titer as a percentage of viral stock are presented in FIG. 5 (linear scale). These data suggest that all of the lumen materials tested had a negative effect on viral efficacy.

In particular, all untreated lumens containing stainless steel (stainless steel per se, stainless steel swaged to nitinol, stainless steel swaged to nitinol with insulated joint and injection catheter) reduced virus activity to only 1–2% of the stock virus titer. Similarly, virus incubated in nitinol retained only 6% of its original activity. Virus incubated within the passivated injection catheter retained 15% of its original activity. 50% of the virus activity was lost post incubation in the polyethylene lumen.

These data suggest that metals such as stainless steel and nitinol result in substantial loss of viral efficacy as compared to polymers, such as polypropylene (control) and polyethylene. The presence of flow in the polymeric and metal lumens versus the lack of flow in the control sample may have negatively impacted virus activity in addition to a detrimental effect as a result of the high surface area to volume ratio with the lumen samples.

Moreover, these data suggest that metal can be passivated by proper chemical treatment. Without wishing to be held to any particular theory, it is believed that the citric acid solution acts to remove free iron and iron oxides and to build up a surface layer compressed primarily of chromium oxides. The resulting surface is non-electrochemically active and is believed to be inert to other chemical and physico-chemical interactions.

It is known that joints between dissimilar metals can create a galvanic reaction in the presence of an electrolyte, resulting in the release of free metal ions and that this may be prevented by insulating the joint between the two metals. Hence, these data also suggest that the loss in efficacy seen with lumens having stainless steel/nitinol joints is not due to a galvanic interaction between nitinol and stainless steel, since the data for insulated and uninsulated joints did not statistically differ.

TABLE

Material compatibility at 30 minutes (stock viral titer 5E+08 pfu/ml)

| Material | Positive cells | Positive cells | Positive cells | Average | Viral titer (pfu/ml) | Std. Dev. | % of stock |
|---|---|---|---|---|---|---|---|
| Control | 430 | | | 430 | 4.30E+08 | | 86 |
| Control* | 38 | 41 | 51 | 43.33 | 4.33E+08 | 6.81E+07 | 108.3 |
| Nitinol | 28 | 40 | 22 | 30 | 3.00E+07 | 9.17E+06 | 6 |
| Stainless steel | 6 | 10 | 6 | 7.33 | 7.33E+06 | 2.31E+06 | 1.47 |
| S.S. swaged to S.S. | 8 | 3 | 6 | 5.67 | 5.67E+06 | 2.52E+06 | 1.13 |
| S.S. swaged to S.S. w/ insulated joint | 5 | 4 | 17 | 8.67 | 8.67E+06 | 7.23E+06 | 1.73 |
| Polyethylene | 240 | 270 | 140 | 216.67 | 2.17E+08 | 6.81E+07 | 43.3 |

TABLE-continued Material compatibility at 30 minutes (stock viral titer 5E+08 pfu/ml)

| Material | Positive cells | Positive cells | Positive cells | Average | Viral titer (pfu/ml) | Std. Dev. | % of stock |
|---|---|---|---|---|---|---|---|
| Injection Catheter* | 4 | 12 | | 8 | 8.00E+06 | 5.66E+06 | 1.86 |
| Passivated injection catheter* | 73 | 40 | 63 | 58.67 | 5.87E+07 | 1.69E+07 | 14.67 |

*Stock viral titer 4E+08 (control at 4.3E+08)

Example 4

Effect of Albumin Flush on Viral Efficacy

The procedure used in this example was similar to that used in Examples 1–3, except that, in addition to an untreated catheter and control, a catheter treated with BSA (bovine serum albumin) was used. The BSA-treated catheter was provided by flushing a catheter with a 1% BSA prior to incubation with virus. The stock virus titer for this example was 5.5E+08 pfu/ml and the incubation time was 30 minutes.

Figure 7:
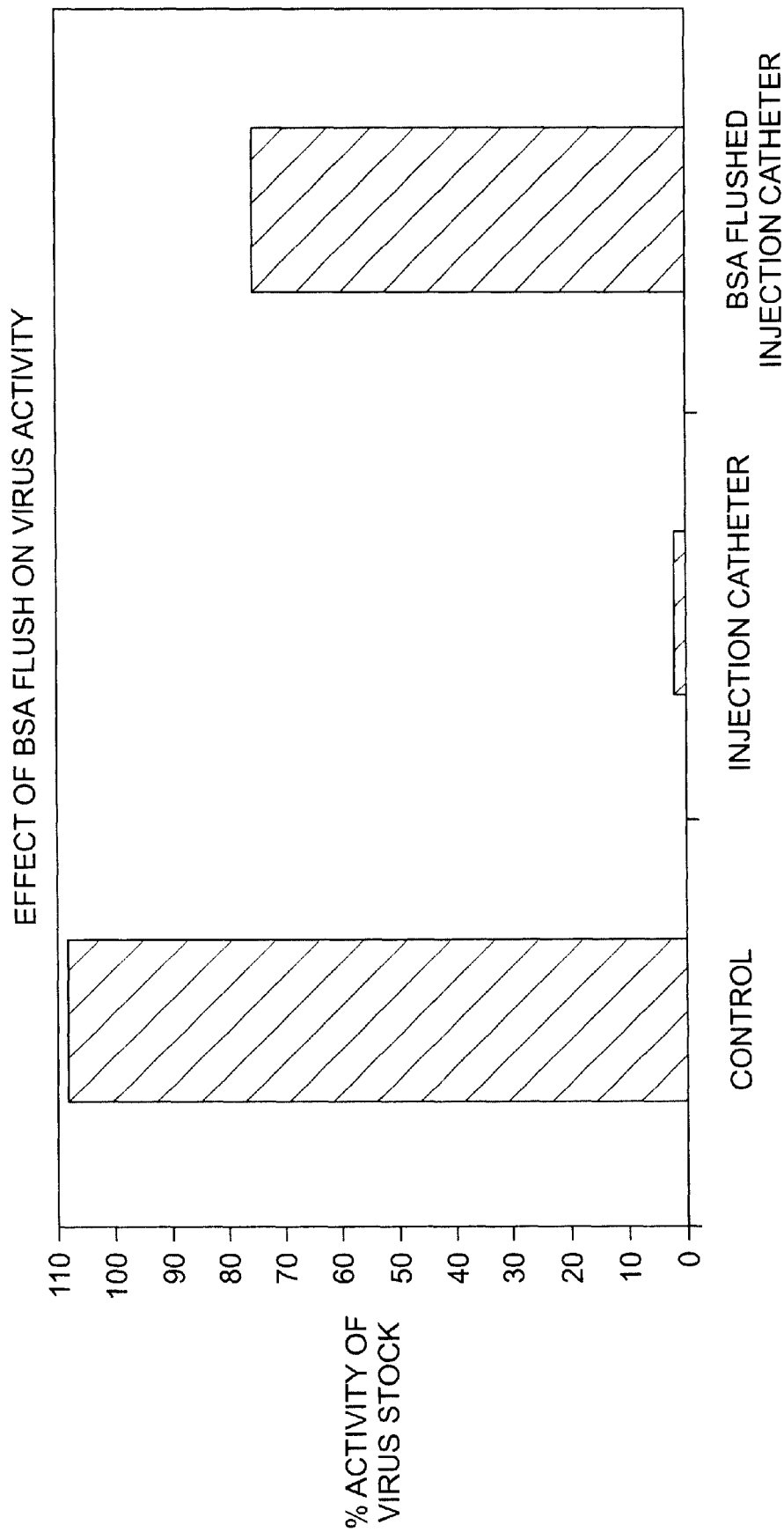
FIG. 7 presents the data of FIG. 6 as a percentage of viral stock titer (linear scale).

Data are presented in the table and FIGS. 6 and 7 to follow. Data in FIG. 6 is absolute titer data (log scale) and data in FIG. 7 is presented as a percentage of virus stock titer (linear scale). Virus incubated in the BSA-treated catheter retained 76% of its efficacy, compared to 2% efficacy for the untreated catheter.

Figure 8:
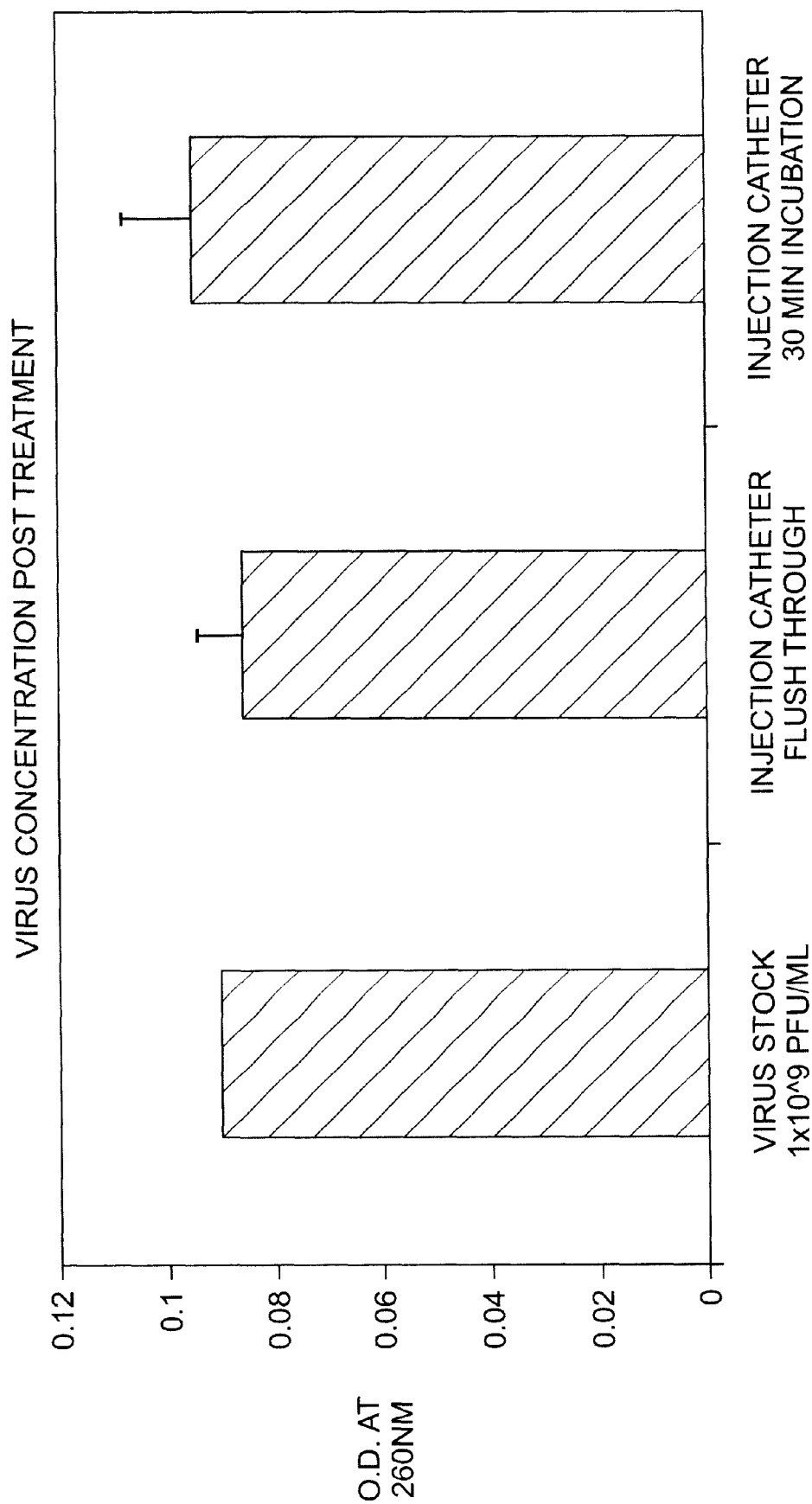
FIGS. 8 and 9 present OD 260 data for (a) virus stock, (b) virus stock after flushing through an injection catheter constructed of stainless steel and nitinol, (c) virus stock after 30 minute incubation in an injection catheter constructed of stainless steel and nitinol, (d) virus stock (e) virus stock after 1:10 dilution, and (f) virus stock after 30 minutes incubation in a polyethylene lumen.

These data suggest that a reduction in viral efficacy in the catheter can be substantially reduced by treatment with BSA. Without wishing to be held to any theory, the albumin may provide a barrier between the metal and virus. Alternatively, dissolved albumin may have a stabilizing effect on the virus in solution. Therefore, the addition of albumin directly to the virus formulation would be expected to exert a similar effect. The resulting effect would be dependent on the concentration of albumin added to the formulation.

data for the virus stock (1E+09 pfu/ml) without exposure to the catheter (control), after flushing through the catheter, and after an incubation time of 30 minutes in the catheter are presented in the following table and in FIG. 8. These data suggest that the concentration of viral particles is effectively the same for samples unexposed to the injection catheter, exposed to the injection catheter during the brief flush-through procedure and exposed to the injection catheter for 30 minutes. These data, in combination with data from Example 1 above, further suggest that the catheter does not retain appreciable amounts of virus, in some fashion (e.g., by adsorption), but rather acts predominantly to inactive the virus.

| | O.D. 260 #1 | O.D. 260 #2 | O.D. 260 #3 | Average | Std. Dev. |
|---|---|---|---|---|---|
| Virus stock (1 × 10^9 pfu/ml) | 0.09 | — | — | 0.09 | — |
| Injection catheter (flush through) | 0.0803 | 0.0808 | 0.0958 | 0.0856 | 0.00881 |
| Injection catheter (30 min incubation) | 0.107 | 0.0801 | 0.0959 | 0.0943 | 0.0135 |

| Material | Pos. cells | Pos. cells | Pos. cells | Average | titer (pfu/ml) | Std. Dev. | % of stock virus |
|---|---|---|---|---|---|---|---|
| Control | 38 | 41 | 51 | 43.3 | 4.33E+08 | 6.81E+07 | 108 |
| Injection Catheter | 4 | 12 | | 8 | 8.00E+06 | 5.66E+06 | 2 |
| BSA flushed injection catheter | 34 | 44 | 48 | 42 | 4.20E+08 | 7.21E+07 | 76 |

Example 5

Viral Adsorption Study

In this example, OD 260 (optical density at a wavelength of 260 nm) data were taken for stock virus, stock virus after 1:10 dilution in PBS, stock virus after flushing it though an injection catheter, stock virus after incubation in an injection catheter for 30 minutes, and stock virus after incubation in polyethylene for 30 minutes. Stock virus titer in this example was 1E+09 pfu/ml.

Figure 9:
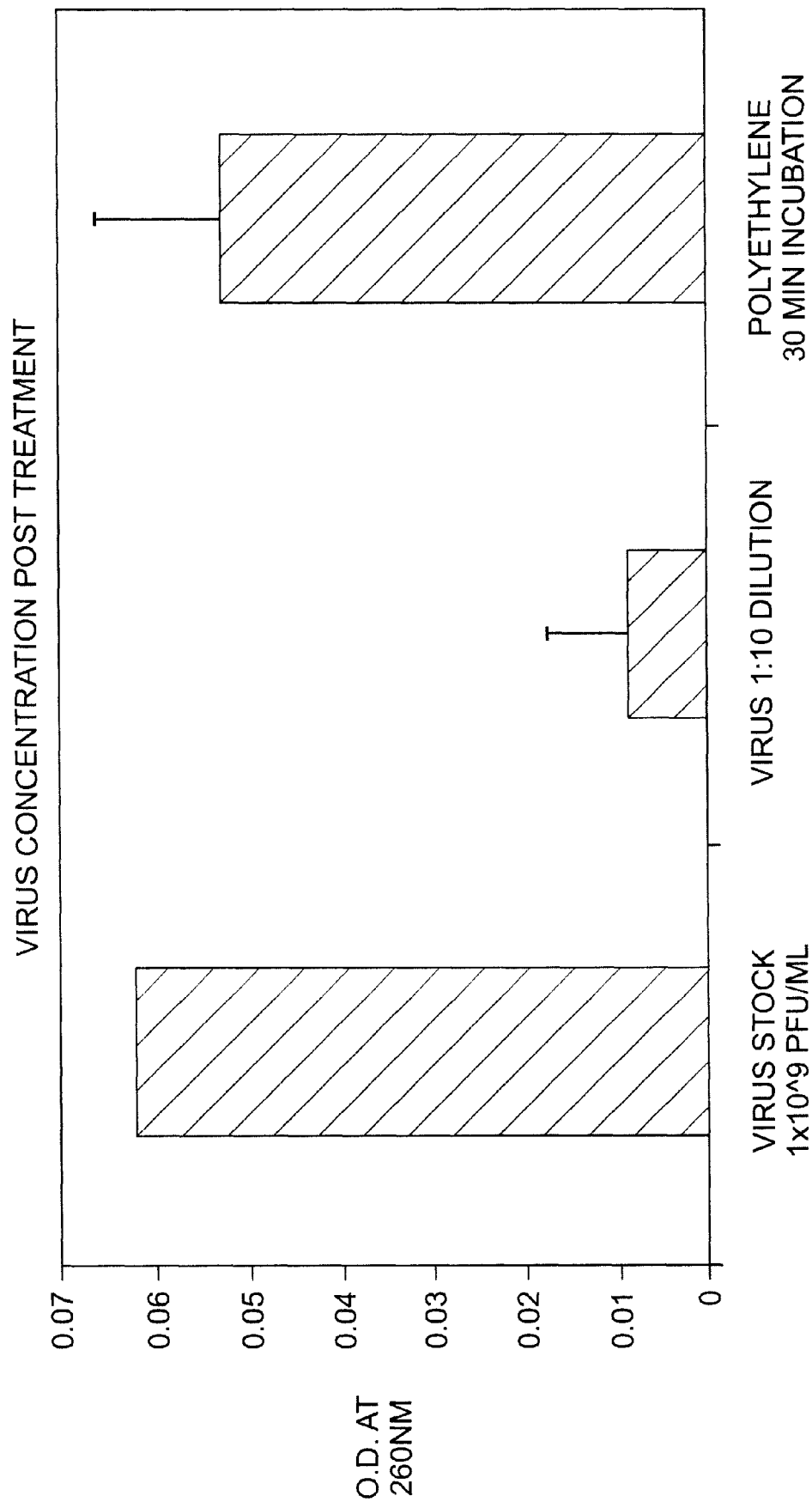

OD 260 provides data related to viral concentration, which data is independent of its biological activity. OD 260 data for the virus stock (1E+09 pfu/ml), for the virus stock at 1:10 dilution (1E+08 pfu/ml), and for the virus stock after incubation in polyethylene for 30 minutes are presented in the following table and in FIG. 9. As expected, the OD 260 after a 1:10 dilution of the virus stock is on the order of one-tenth that of the undiluted virus stock. Moreover, the differences between the OD 260 of the virus stock and the virus stock after 30 minutes in polyethylene, while different, do not appear to be statistically different. These data, in combination with data from Example 3 above, suggest that polyethylene retains little, if any, virus (e.g., by adsorption), but rather acts to inactivate the virus.

|  | O.D. 260 #1 | O.D. 260 #2 | O.D. 260 #3 | Average | St. Dev. |
|---|---|---|---|---|---|
| virus stock ($1 \times 10^9$ pfu/ml) | 0.0618 | — | — | 0.0618 | — |
| virus (1:10 dilution) | 0.0084 | — | — | 0.0084 | — |
| Polyethylene (30 min incubation) | 0.063 | 0.0486 | 0.0457 | 0.0524 | 0.00926 |

The above data suggest, inter alia, (1) that metals such as stainless steel and nitinol have an adverse effect upon the activity of a pharmaceutically active material such as an adenovirus vector, (2) that the metals can be treated to reduce this adverse effect, and (3) that this adverse effect is based on inactivation of the pharmaceutically active material, rather than adsorption.

The present invention provides methods and devices for the delivery of pharmaceutically active materials that overcome incompatibility problems of the prior art. Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

We claim:

1. An injection catheter for delivery of a pharmaceutically active material, said injection catheter comprising: a metallic lumen, said metallic lumen acting to substantially reduce pharmaceutical effectiveness of said pharmaceutically active material upon contact; wherein said metallic lumen is further provided with a layer of polymeric material that comprises a polymer selected from a silicone polymer, a polypropylene, and a polyether block amide such that said substantial reduction in the pharmaceutical effectiveness of the pharmaceutically active material is decreased.

2. The injection catheter of claim 1, wherein said injection catheter is an intravascular injection catheter having an injection lumen.

3. The injection catheter of claim 1, wherein said injection catheter is a percutaneous myocardial revascularization catheter.

4. The injection catheter of claim 1, wherein said lumen comprises stainless steel or nitinol.

5. The injection catheter of claim 1, further comprising said pharmaceutically active material, wherein the pharmaceutically active material comprises a polynucleotide, a protein or whole cells.

6. The injection catheter of claim 1, wherein said layer of polymeric material is provided by coating the metallic lumen with uncured polymer, and curing said uncured polymer.

7. The injection catheter of claim 1, wherein said layer of polymeric material comprises a silicone polymer.

8. The injection catheter of claim 1, wherein said layer of polymeric material comprises a polyether block amide.

9. The injection catheter of claim 1, wherein the layer of polymeric material is provided in the form of a preformed tube.

10. The injection catheter of claim 5, wherein the pharmaceutically active material comprises a polynucleotide.

11. The injection catheter of claim 5, wherein the pharmaceutically active material comprises whole cells.

12. The injection catheter of claim 10, wherein the pharmaceutically active material comprises naked DNA.

13. The injection catheter of claim 10, wherein the pharmaceutically active material comprises a viral vector.

14. The injection catheter of claim 13, wherein the viral vector is an adenoviral vector.

15. The injection catheter of claim 14, wherein said layer of polymeric material comprises a polypropylene.

\* \* \* \* \*